United States Patent
Brask et al.

(10) Patent No.: US 10,881,783 B2
(45) Date of Patent: Jan. 5, 2021

(54) PROCESSING INFUSION PUMP DATA FOR PRESENTATION ON OPERATOR INTERFACE

(71) Applicant: Fenwal, Inc., Lake Zurich, IL (US)

(72) Inventors: David Brask, Mundelein, IL (US); Thomas Karakosta, Chicago, IL (US); Witold Moskal, Park Ridge, IL (US); Maciej Wroblewski, Glenview, IL (US)

(73) Assignee: Fenwal, Inc., Lake Zurich, IL (US)

( * ) Notice: Subject to any disclaimer, the term of this patent is extended or adjusted under 35 U.S.C. 154(b) by 500 days.

(21) Appl. No.: 15/337,030

(22) Filed: Oct. 28, 2016

(65) Prior Publication Data
US 2017/0143895 A1 May 25, 2017

Related U.S. Application Data

(60) Provisional application No. 62/257,889, filed on Nov. 20, 2015.

(51) Int. Cl.
*G06Q 50/22* (2018.01)
*A61M 5/142* (2006.01)
(Continued)

(52) U.S. Cl.
CPC ......... *A61M 5/142* (2013.01); *G06F 19/3468* (2013.01); *G16H 15/00* (2018.01);
(Continued)

(58) Field of Classification Search
CPC ............... A61M 5/142; A61M 5/16854; G06F 19/3481; G06F 19/326; G06Q 50/00
(Continued)

(56) References Cited

U.S. PATENT DOCUMENTS 7,835,927 B2 * 11/2010 Schlotterbeck ........ G06Q 50/22
   705/3
8,150,709 B2 * 4/2012 Miller ................... G16H 10/40
   705/2
(Continued)

FOREIGN PATENT DOCUMENTS

| EP | 2336924 A1 | 6/2011 |
| WO | WO2004061745 A2 | 7/2004 |
| WO | WO2004072828 A2 | 8/2004 |

OTHER PUBLICATIONS

Google patents search, Jan. 29, 2019 (Year: 2019).*
(Continued)

*Primary Examiner* — Dilek B Cobanoglu
(74) *Attorney, Agent, or Firm* — Becker Patent Law, LLC

(57) ABSTRACT

A server computer processes infusion pump data for presentation on an operator interface. The computer includes a network circuit configured to provide communications over a network and a processing circuit. The processing circuit receives infusion pump history data from a plurality of infusion pumps, including an indication that a user inputted to an infusion pump a parameter which was outside of a prestored limit, an indication that a user was notified that the parameter was outside the prestored limit, an indication that the infusion pump parameter was returned to within the prestored limit, and an indication that the user started infusion on the pump at the parameter within the prestored limit. Display data indicating reprogram and override events is generated for display on an operator interface.

9 Claims, 12 Drawing Sheets

(51) Int. Cl.
*G16H 15/00* (2018.01)
*G06F 19/00* (2018.01)

(52) U.S. Cl.
CPC ............ *A61M 2005/14208* (2013.01); *A61M 2205/3584* (2013.01); *A61M 2205/502* (2013.01); *A61M 2205/52* (2013.01)

(58) Field of Classification Search
USPC .............................. 705/3, 2; 604/508; 700/89
See application file for complete search history.

(56) References Cited

U.S. PATENT DOCUMENTS

| | | | |
|---|---|---|---|
| 8,271,106 B2* | 9/2012 | Wehba | G16H 20/17 |
| | | | 700/89 |
| 8,380,536 B2 | 2/2013 | Howard et al. | |
| 9,069,887 B2* | 6/2015 | Gupta | G06F 19/3418 |
| 9,741,001 B2* | 8/2017 | Gupta | G16H 20/13 |
| 2005/0055242 A1 | 3/2005 | Bello et al. | |
| 2009/0156991 A1* | 6/2009 | Roberts | G16H 40/40 |
| | | | 604/67 |
| 2012/0185267 A1* | 7/2012 | Kamen | A61B 5/0024 |
| | | | 705/2 |
| 2013/0047113 A1 | 2/2013 | Hume et al. | |
| 2013/0297330 A1* | 11/2013 | Kamen | G06F 19/3462 |
| | | | 705/2 |
| 2014/0180711 A1 | 6/2014 | Kamen et al. | |
| 2015/0306310 A1* | 10/2015 | Tsoukalis | G08B 21/182 |
| | | | 604/508 |

OTHER PUBLICATIONS

Google patents search, Dec. 28, 2019 (Year: 2019).*
A.C. Catlin et al., "Comparative analytics of infusion pump data across multiple hospital systems," American Journal of Health-System Pharmacy, vol. 72, No. 4, Jan. 28, 2015 (Jan. 28, 2015), pp. 317-324.
Kastrup Marc et al., "Analysis of event logs from syringe pumps: a retrospective pilot study to assess possible effects of syringe pumps on safety in a university hospital critical care unit in Germany," Drug Saf, Adis Press, Auckland, NZ, vol. 35, No. 7, Jul. 1, 2012 (Jul. 1, 2012), pp. 563-574.
European search report and opinion, App. No. 16197013.2-1871/3171287, dated Sep. 7, 2017, 10 pages.
EP Communication and Annex in App. No. 16197013.2, dated Feb. 12, 2020, 4 pages.

* cited by examiner

FIG. 2

| OVERRIDE | A START OF INFUSING WITH DRUG PARAMETERS OUTSIDE OF DEFINED LIMITS. |
|---|---|

```
                    ┌42
─────────────────────○──────────────────── UPPER HARD LIMIT
                      CONFIRM PARAMETERS→LIMIT ALERT→CONFIRM
─────────────────────────────────────────── UPPER SOFT LIMIT    PARAMETERS
    40─┐        ┌44                                                  ↓
        ○        ○───SELECT DRUG                                  START
   ↑                                                              INFUSION
SELECT DRUG
─────────────────────────────────────────── LOWER SOFT LIMIT
          46 ┐○  CONFIRM PARAMETERS→LIMIT ALERT→CONFIRM
─────────────────────────────────────────── LOWER HARD LIMIT    PARAMETERS
                                                                     ↓
                                                                START INFUSION
```

| REPROGRAM | CONFIRM THE DRUG PARAMETERS OUTSIDE OF DEFINED LIMITS. AFTER AN OVERRIDE ALERT IS DISPLAYED, RETURN DRUG PARAMETERS TO BE WITHIN THE DEFINED LIMITS THEN STARTING AN INFUSION. |
|---|---|

```
                    ┌52
─────────────────────○──────────────────── UPPER HARD LIMIT
                      CONFIRM PARAMETERS→LIMIT ALERT
─────────────────────────────────────────── UPPER SOFT LIMIT
                  54┐○ START INFUSION
       ○─50         ○───SELECT DRUG
   SELECT DRUG           ○ START INFUSION
─────────────────────────────────────────── LOWER SOFT LIMIT
                         ○ CONFIRM PARAMETERS→LIMIT ALERT
─────────────────────────────────────────── LOWER HARD LIMIT
```

| DRUG LIMIT | DRUG LIMIT: SERVER STORES FOUR TYPES OF LIMITS FOR EACH DRUG: UPPER HARD LIMIT, UPPER SOFT LIMIT, LOWER HARD LIMIT, AND LOWER SOFT LIMIT. |
|---|---|
| DATASET | A RULE SET THAT DEFINES UPPER / LOWER SOFT / HARD LIMITS FOR KNOWN DRUG TO BE INFUSED |

REPORTS INFUSION RECORD

| | | | |
|---|---|---|---|
| 10/29/2015 | 5:12PM | USER PAUSE | DOSE RATE=2MCG/MIN<br>DOSE INFUSED=0MG<br>CALCULATED DURATION=0 SECONDS |
| 10/29/2015 | 5:12PM | PRIMARY INFUSION STOP | VOLUME INFUSED=2.589ML<br>FLOW RATE=720 ML/H<br>DOSE RATE=2 MCG/MIN<br>DOSE INFUSED=0 MG<br>ACTUAL DURATION=14 SECONDS |
| 10/29/2015 | 5:12PM | PRIMARY INFUSION: CROSS BELOW LOWER SOFT LIMIT (LSL) ⟵ 60 | LIMIT VALUE=1MCG/MIN |
| 10/29/2015 | 5:12PM | PRIMARY INFUSION: OVERRIDE BELOW LOWER SOFT LIMIT (LSL) START ⟵ 62 | CONFIRMED VALUE=<br>0.01 MCG/MIN |
| 10/29/2015 | 5:12PM | PRIMARY INFUSION: CONFIRMED VALUE OUTSIDE SOFT LIMITS ⟵ 64 | LIMIT 1.000 MCG/MIN |
| 10/29/2015 | 5:12PM | PRIMARY INFUSION START | FLOW RATE=3.6 ML<br>VOLUME TO INFUSE=2.597ML<br>DOSE RATE=0.01 MCG/MIN<br>DOSE INFUSED=0 MG<br>CALCULATED DURATION=2597 SECONDS |
| 10/29/2015 | 5:15PM | PRIMARY INFUSION: OVERRIDE BELOW LOWER SOFT LIMIT (LSL) END ⟵ 66 | CONFIRMED VALUE=0.01 MCG/MIN<br>LIMIT VALUE=1.000 MCG/MIN |
| 10/29/2015 | 5:15PM | PRIMARY INFUSION STOP | ACTUAL DURATION=198 SECONDS |
| 10/29/2015 | 5:15PM | USER INITIATED END OF PRIMARY INFUSION | |
| 10/29/2015 | 5:15PM | END OF INFUSION ⟵ 68 | |

FIG. 3

| | | |
|---|---|---|
| 11/17/2015 8:04PM USER PAUSE | | |
| 11/17/2015 8:04PM PRIMARY INFUSION STOP | | VOLUME INFUSED=0.309ML<br>FLOW RATE=12ML/H<br>DOSE RATE=2 MCG/MIN<br>DOSE INFUSED=0.003MG<br>ACTUAL DURATION=92 SECONDS |
| 11/17/2015 8:04PM PRIMARY INFUSION: CROSS ABOVE UPPER SOFT LIMIT (USL) | | LIMIT VALUE=4 MCG/MIN |
| 11/17/2015 8:04PM PRIMARY INFUSION: REPROGRAM ABOVE UPPER SOFT LIMIT (USL) | ⟵70 | LIMIT VALUE=4 MCG/MIN |
| 11/17/2015 8:04PM PRIMARY INFUSION: CONFIRMED VALUE OUTSIDE SOFT LIMITS | | LIMIT VALUE=4 MCG/MIN |
| 11/17/2015 8:05PM PRIMARY INFUSION: CROSS ABOVE UPPER SOFT LIMIT (USL) | | LIMIT VALUE=4 MCG/MIN |
| 11/17/2015 8:05PM PRIMARY INFUSION: CROSS BELOW UPPER SOFT LIMIT (USL) | 72⟵ | LIMIT VALUE=4 MCG/MIN |
| 11/17/2015 8:05PM PRIMARY INFUSION START | 74⟵ 76⟵ | FLOW RATE=23.4ML/H<br>VOLUME INFUSED=0.31ML<br>VOLUME TO INFUSE=499.69<br>DOSE RATE=3.9 MCG/MIN<br>DOSE INFUSED=0.003 MG<br>CALCULATED DURATION=76875 SECONDS |
| 11/17/2015 8:05PM USER PAUSE | | |

FIG. 4

| REPORTS > OVERRIDE LISTING | | | | | | | | |
|---|---|---|---|---|---|---|---|---|
| REPORT TYPE : OVERRIDE LISTING ⌄ | | | FROM : 30 DAYS ☐ | | TO : TODAY ☐ | | EXPORT | |
| HOSPITAL : ALL ⌄ | | VIGILANT DATA SET : ALL ⌄ | | PROFILE : ALL ⌄ | | DRUG : ALL ⌄ | | |
| DEVICE TYPE : ALL ⌄ | | INFUSION MODE : ALL ⌄ | | | | 63790 TOTAL OVERRIDES | | |
| START TIME | END TIME | HOSPITAL | DATA SET | PROFILE | DRUG | OVERRIDE | | |
| 6/15 2015 2:45 PM | 6/15 2015 2:27 PM | ROYAL INFIRMARY | DATASET 12 | PEDS 19KG OR BELOW | DOPAMINE | LOADING DOSE: OVERRIDE BELOW LOWER SOFT LIMIT (LSL) | | |
| 6/15 2015 2:45 PM | 6/15 2015 2:34 PM | FIFE | DATASET 12 | PEDS 19KG OR BELOW | DOPAMINE | LOADING DOSE: OVERRIDE BELOW LOWER SOFT LIMIT (LSL) | | |
| 6/15 2015 2:45 PM | 6/15 2015 2:34 PM | FORTH VALLEY | DATASET 12 | PEDS 19KG OR BELOW | DOPAMINE | LOADING DOSE: OVERRIDE BELOW LOWER SOFT LIMIT (LSL) | | |
| 6/15 2015 2:45 PM | 6/15 2015 2:37 PM | ROYAL INFIRMARY | DATASET 12 | PEDS 19KG OR BELOW | DOPAMINE | LOADING DOSE: OVERRIDE BELOW LOWER SOFT LIMIT (LSL) | | |
| 6/15 2015 2:45 PM | 6/15 2015 2:46 PM | ROYAL INFIRMARY | DATASET 12 | PEDS 19KG OR BELOW | DOPAMINE | LOADING DOSE: OVERRIDE BELOW LOWER SOFT LIMIT (LSL) | | |

FIG. 5

REPORTS > REPROGRAM LISTING

| REPORT TYPE : REPROGRAM LISTING ⌄ | | | | | FROM : 30 DAYS ☐ | TO : TODAY ☐ | EXPORT |
|---|---|---|---|---|---|---|---|

106

| HOSPITAL : ALL ⌄ | | VIGILANT DATA SET : ALL ⌄ | | PROFILE : ALL ⌄ | DRUG : ALL ⌄ | |
|---|---|---|---|---|---|---|
| DEVICE TYPE : ALL ⌄ | | INFUSION MODE : ALL ⌄ | | | | |

10900 TOTAL OVERRIDES
104

| START TIME | HOSPITAL | DATA SET | PROFILE | DRUG | REPROGRAM |
|---|---|---|---|---|---|
| 6/15 2015 2:45 PM | SALISBURY | DATASET 12 | PEDS 19KG OR BELOW | DOPAMINE | LOADING DOSE: REPROGRAM ABOVE UPPER SOFT LIMIT (USL) |
| 6/15 2015 2:45 PM | SALISBURY | DATASET 12 | PEDS 19KG OR BELOW | DOPAMINE | LOADING DOSE: REPROGRAM ABOVE UPPER SOFT LIMIT (USL) |
| 6/15 2015 2:45 PM | ROYAL MARSDEN | DATASET 12 | PEDS 19KG OR BELOW | DOPAMINE | LOADING DOSE: REPROGRAM ABOVE UPPER SOFT LIMIT (USL) |
| 6/15 2015 2:45 PM | ROYAL BERKSHIRE | DATASET 12 | PEDS 19KG OR BELOW | DOPAMINE | LOADING DOSE: REPROGRAM ABOVE UPPER SOFT LIMIT (USL) |
| 6/15 2015 2:45 PM | ROYAL BERKSHIRE | DATASET 12 | PEDS 19KG OR BELOW | DOPAMINE | LOADING DOSE: REPROGRAM ABOVE UPPER SOFT LIMIT (USL) |

REPORTS > HARD LIMIT OVERRIDE LISTING

REPORT TYPE : HARD LIMIT OVERRIDE LISTING ⌄     FROM : 30 DAYS 🗓    TO : TODAY 🗓    EXPORT

HOSPITAL : ALL ⌄    VIGILANT DATA SET : ALL ⌄    PROFILE : ALL ⌄    DRUG : ALL ⌄

DEVICE TYPE : ALL ⌄    INFUSION MODE : ALL ⌄

START TIME ⌄    HOSPITAL    DATA SET    PROFILE    DRUG    HARD LIMIT

NO RESULTS MATCHED REPORT CRITERIA

FIG. 7

PROCESSING INFUSION PUMP DATA FOR PRESENTATION ON OPERATOR INTERFACE

CROSS REFERENCE TO RELATED APPLICATIONS

This application claims the benefit of U.S. Provisional App. No. 62/257,889, filed Nov. 20, 2015, which is incorporated by reference herein in its entirety.

BACKGROUND

Infusion pumps are used to administer drugs and other medicaments to patients, typically in a clinical setting. An infusion pump provides a controlled amount of the medicament over time to the patient. The amount is administered pursuant to parameters entered by a clinician into the pump using a pump user interface.

To avoid errors in drug administration, some infusion pumps hold a library of drug names and associated parameters. For example, a drug may have a hard upper limit for a parameter such as rate of infusion. The hard upper limit is predetermined by a pharmacist or other clinician familiar with the drug. When a user selects the drug and programs a rate of infusion, the infusion pump prevents the pump from being programmed to administer the drug above the hard upper limit. In another example, a drug may have a soft upper limit. When a user selects the drug and attempts to program the rate of infusion above the soft upper limit, an alert is given on the user interface to notify the user they are requesting a parameter beyond the soft upper limit and asking the user to confirm the rate of infusion.

The drug library may be created—and updated—by a pharmacist. In some cases, nurses or other clinicians who use the pump have knowledge of drug parameters useful in certain care areas that the pharmacist may not. This leads to frequent overriding or reprogramming of limits programmed into the drug library by the pharmacist. This impacts efficiency of clinical staff and effectiveness of the use of hard and soft limits.

BRIEF DESCRIPTION OF THE DRAWINGS

FIG. 2 is an illustration of exemplary hard and soft limits and their override or reprogramming;

FIG. 3 is a display screen of infusion records showing illustrative override events;

FIG. 4 is a display screen of infusion records showing illustrative reprogram events;

FIG. 5 is a display screen of an override listing report, according to an illustrative embodiment;

FIG. 6 is a display screen of a reprogram listing report, according to an illustrative embodiment;

FIG. 7 is a display screen of a hard limits override listing report, according to an illustrative embodiment;

DETAILED DESCRIPTION OF ILLUSTRATIVE EMBODIMENTS

One or more embodiments described herein may facilitate analysis of infusion events to help pharmacy and nursing staff to report drug parameters outside of defined limits.

One or more embodiments described herein may identify issues with drug limits within Dose Error Reduction Systems (DERS).

One or more embodiments described herein may improve clinical procedure and help to train nursing staff to use DERS effectively.

One or more embodiments described herein may identify drug parameters outside of defined limits.

One or more embodiments described herein may provide automated analysis instead of requiring a pharmacy to analyze data by hand.

One or more embodiments described herein may help evaluate if drug limits defined for a drug should be adjusted in a DERS.

One or more embodiments described herein may help with deciding if the current clinical procedure should be changed.

Figure 1:
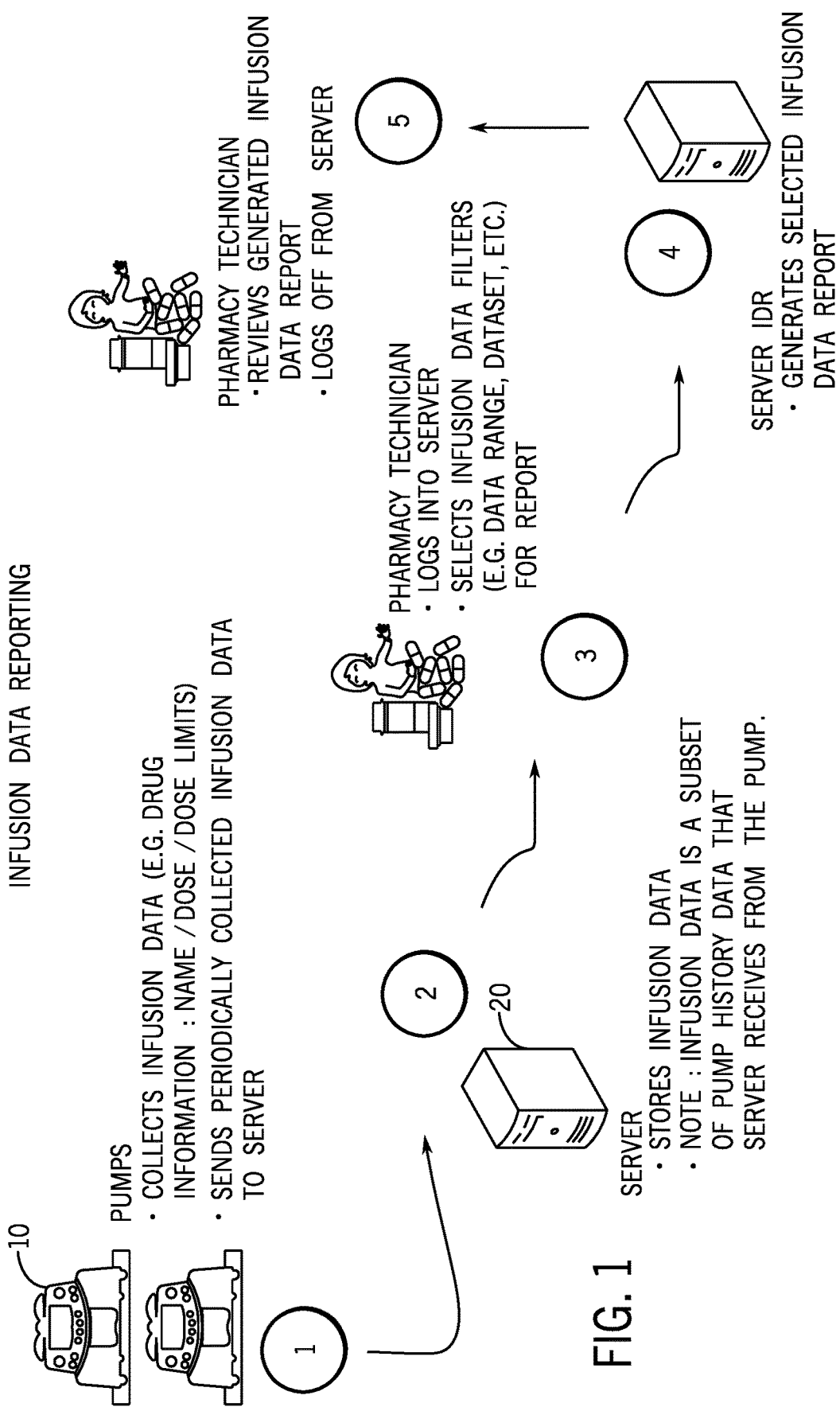
FIG. 1 is a flow diagram of a system for collecting infusion data from a plurality of infusion pumps at a server computer, according to an illustrative embodiment.

Referring now to FIG. 1, a flow diagram of a system for collecting infusion data from a plurality of infusion pumps at a server computer will be described. Infusion pump 10 may be any of a variety of infusion pumps, such as a large volume infusion pump, a patient-controlled analgesia (PCA) pump, elastomeric pump, syringe pump, enteral or parenteral feeding pump, insulin pump, etc. At Step 1 in FIG. 1, infusion pump 10 is configured to collect infusion pump history data, such as user key presses on a user interface thereof, alarm data, etc. History data can include drug name, dose, dose changes, start time, stop time, alarm information, cross beyond hard or soft upper or lower limits, etc. Alarm data may include a type of alarm, a start time for the alarm, a care area in which the pump was used during the alarm, a drug name of a drug being administered during the alarm, time to alarm resolution, etc.

At Step 2 in FIG. 1, infusion pump 10 may be configured for wired and/or wireless communication with a server computer 20. Each of pump 10 and server computer 20 may comprise a network interface circuit configured for network communications, such as a Wi-Fi circuit, Bluetooth circuit, Ethernet card, or other network interface circuit. Pump 10 is configured to transmit and server 20 is configured to receive infusion pump data over the respective network interface circuits. Server 20 is configured to store the infusion data from a plurality of infusion pumps, which may be in different care areas, for analysis, whether automated or by a clinician. Care areas may include rooms, wards, floors, or other portions of a patient care facility dedicated to a particular type of care, such as intensive care unit, neonatal intensive care unit, ambulatory care unit, memory care area, surgery, primary care, etc. Infusion data transmissions may be initiated by infusion pump 10 and may occur periodically, intermittently, occasionally, every few minutes, several times per day, or at other regular or irregular frequencies. Infusion data stored at server 20 may be a subset of pump history data that server 20 receives from pump 10.

At Step 3 in FIG. 1, a nurse, pharmacist, biomedical engineering staff, or other user may log into server 20 using a terminal (not shown), which may be a user interface for server 20 or may alternatively be a separate computing device or PC. The user opens an application configured to review infusion pump data. Server 20 may be configured to generate one or more reports based on analysis of the infusion pump history data. Reports may be generated in a prescheduled manner or on-demand based on user inputs to the system. Reports may also be sent automatically, without requiring user input, on a scheduled basis, or in response to certain rules being met (e.g., alarm triggered, a certain number of alarms triggered, a certain number of override or reprogram events, etc.). The user may select one or more infusion data filters, such as hospital, data set, profile, drug, device type, infusion mode, time and/or date range, etc.

At Step 4 in FIG. 1, the server computer is configured to generate the selected infusion data report or reports.

At Step 5 in FIG. 1, a user analyzes the report data and may make changes to a data set or library used to program infusion pumps 10. For example, a data set may comprise hard limits and/or soft limits to different pump programming parameters, such as infusion rate, dose, infusion time or duration, etc. The limits of the data set may be different for different drugs, and may include a "drug X" data set for a drug not known by the data library. Once changes are made to the data set or library, server 20 may be used to remotely download, update, or otherwise program infusion pumps 10 (e.g., by care area, universally, etc.) with the new data set changed by the pharmacist or other user at Step 4.

Referring now to FIG. 2, an illustration of pump history data is provided. Each box 40, 42, 44, etc. represents one or more pump history data elements or events which may be independently reported from the infusion pump 10 to the server 20. For example, box 40 represents an indication that a user selected a drug from a list or library of drugs on the infusion pump, which includes the name of the drug selected. Box 40 also represents an initial value of the pump parameter which is within upper and lower limits and which is changeable by a user (e.g., by scrolling up/down using buttons, touch screen, or other input mechanism). Box 42 indicates that the user inputted to the infusion pump a parameter which was outside of a prestored limit, namely an upper soft limit. Infusion pump 10 then provided an indication that the parameter was outside the upper soft limit ("LIMIT ALERT"). Infusion pump 10 then received an indication from the user that the input value was confirmed ("CONFIRM PARAMETERS") and an indication that the infusion was started ("START INFUSION"). Each of these indications can be a separate pump history data element stored in memory of the pump 10 and reported separately or in a batch to server 20.

In this embodiment, server 20 is configured to build or determine the existence of certain events or conditions, such as an "override" event, a "reprogram" event, or other event, based on the basic, individual or discrete history data elements or events reported from pump 10. This advantageously allows the characteristics of the events to be changed at the server computer 20 without requiring a reprogramming of individual infusion pumps. In an alternative embodiment, a single data element from pump 10 may represent a plurality of these base events or indications. For example, pump 10 may conclude that an override event has occurred based on the indications of a parameter outside an upper soft limit and a confirmation and infusion start event, which the pump 10 may report as a single "override soft limit" event to server 20.

A hard limit may refer to a limit beyond which pump 10 does not allow a user to set a value of a parameter. A soft limit may refer to a limit beyond which a pump 10 does allow a user to set a value of parameter, only after the user has been notified that the value is outside of the soft limit. A pharmacist may program hard and soft limits for different drugs in a drug library in order to guide a nurse, clinician or other user when programming parameters into infusion pump 10. Blocks 40-42 and 44-46 may be referred to as override events, because the history data comprises an indication that a user started infusion on the pump at the parameter which was outside of the prestored soft limit, or at the prestored hard limit. The existence of an override limit may be determined by server 20 based on individual pump history data elements received, or by pump 10.

An exemplary reprogram event is also illustrated in FIG. 2. Block 50 represents an infusion pump history data element comprising an indication that a user selected a particular drug from the library. The initial value of the pump parameter may be a default parameter, for example a parameter from a previous infusion, a pre-programmed default value from the dataset/library, etc. Block 52 represents an indication that a user inputted to an infusion pump a parameter which was outside of a prestored limit, namely an upper soft limit. Block 52 also represents an indication that the pump provided a confirmation or alert ("LIMIT ALERT") to the user and requested confirmation. Block 54 represents an indication that the user returned the infusion pump parameter to within the prestored limit and the user started the infusion at the parameter within the prestored limit. A similar illustration is provided for a reprogram event for a lower soft limit. A reprogram event may refer to a confirmation that a drug parameter is outside of a predefined limit, such as an upper soft limit, that an alert or notification is provided, that the parameter is returned to be within the predefined limits, and that the infusion is then started.

FIG. 3 is a display screen of infusion records showing illustrative override events. This display screen may be shown at a location remote from infusion pump 10, for example at a display in communication with server 20 via a web based user interface. A field 60 of the display provides an indication that a server algorithm recognized a sequence of basic events that created an override event. In this case, a date and time of the override event is provided along with an indication that a pump programming value was input below a lower soft limit during a primary infusion. The values of a comparison are shown as confirmed value=0.01 mcg/min and limit value=1000 mcg/min. A field 61 shows that a user programmed a value (e.g., by scrolling the value) into pump 10 that crossed below the lower soft limit (LSL). A field 62 shows that the user confirmed the value outside of the soft limit, including again the date/time, event description and the value which was confirmed. A field 64 shows that a primary infusion was started, including date/time, as well as some additional parameters regarding the infusion, such as flow rate, volume to infuse, dose rate, dose infused and calculated duration of infusion. Data elements 61, 62 and 64 are pump history data received by server 20 from infusion pump 10. Element 60 is generated by a server algorithm. Additional events are shown, such as an end of the infusion below the lower soft limit (field 66) and an end of the infusion (field 68).

FIG. 4 is a display screen of infusion records showing an illustrative reprogram event. At a field 70, an indication is shown that a user inputted to an infusion pump (e.g., via a scrollable input or other input device) a parameter which was outside of a prestored limit. Specifically, the value of the parameter crossed above the upper soft limit of 4 mcg/h. At field 72, there is an indication that the pump confirmed to the user that the drug parameter was outside the limit, which may be provided as an alert. This confirmation may include a message, notification, prompt or other indication provided on a screen of the infusion pump 10. In one example, the user is provided with a full screen alert on the pump, which may further comprise a change of color of one or more screen or display elements (e.g., LEDs near the screen, portions of the screen), a buzzer or other audible alarm, etc. The confirmation may further include a textual display indicating the value is outside the limit and a question as to whether the user wishes to proceed with that value and/or whether the user wishes to return to a value within the limit (which value may also be displayed for user selection). At field 74, there is an indication that the user returned the drug parameter to within the limit. At field 76, there is an indication that the user started infusion on the pump to start the infusion at the parameter within the prestored limit (e.g., at a Dose Rate of 3.9 mcg/min in this example). Field 76 shows additional pump history data associated with the event, namely a flow rate, a volume infused, a volume to infuse, a dose rate, a dose infused, and a calculated duration the infusion will take. Note the display of the indications of events may or may not be sorted chronologically in different embodiments.

The pump history data illustrated in FIGS. 3 and 4 need not be displayed in all embodiments. In some embodiments, this pump history data is received from one or more pumps and stored in memory of server 20 for analysis.

FIG. 5 is a display screen of an override listing report, according to an illustrative embodiment. The override listing report may display a list of soft limit overrides with one or more of the following information for each override: Override Start Time 80, Override End Time 82, Location of pump that generated Override 84, Dataset used when Override occurred 86, Selected Profile used when Override occurred 88, Drug used when Override occurred 90 and a description of the Override itself 92. In one example, server 20 is configured to analyze the infusion pump history data described above with reference to FIG. 3 to determine that an override event has occurred. For example, server 20 may determine that a pump parameter was programmed outside of a soft limit, an alert or notification was provided, the parameter was confirmed by the user, and the infusion was started. Server 20 may be configured to determine based on this collection or series of events that an override event has occurred, and server 20 may be configured to generate a record in memory comprising one or more of data elements 80-92 regarding the override event.

FIG. 5 illustrates useful features that allow a pharmacist or other user to sort, filter, and/or display the data in a manner that allows the pharmacist to make conclusions about how and when overrides are occurring. These conclusions can assist the pharmacist in making future revisions to drug libraries for pumps. For example, a time filter input field 94 which allows the user to filter the override listing based on a selected period of time (e.g., prior 30 days to today, prior 30 days to an input date, etc.). A report type input device 96 allows a user to select among different report types, such as an override listing (FIG. 5), a reprogram list report (FIG. 6), a hard limit override listing report (FIG. 7), etc. Additional filter input fields 98 allow a user to filter based on other data elements, such as hospital 84, data set 86, profile 88, drug 92, device type, infusion mode, etc. In one example, an override listing 100 indicates that an override below a lower soft limit (LSL) occurred at a certain date and time at Forth Valley hospital on a pump that was running Dataset 12 with a profile of pediatric patients 19 kg or below for the drug Dopamine. One of the data fields, such as Override Start Time, may be selectable to navigate to the detailed infusion record during which the override event occurred.

FIG. 6 is a display screen of a reprogram listing report, according to an illustrative embodiment. This display screen comprises similar features to that of FIG. 5, such as time filter input field, filter and sort functions. FIG. 6 displays reprogram events determined by server 20. For example, at field 102, server 20 has determined that a reprogram event occurred at a certain date and time at the Royal Mardsen hospital on a pump using Dataset 12 programmed with a profile of pediatric 19 kg or below for the drug dopamine. The reprogram event was a reprogram of a loading dose above an upper soft limit. A total reprograms field 104 displays an indication of the total number of reprogram events server 20 has stored and that are available for viewing using the various filters provided. An Export button 106 allows a user to export the selected report to a file for electronic transmission, sharing, printing, etc. In another aspect, one of the fields, such as Reprogram Time, may be selectable (e.g., via a hyperlink or other selectable input device) to navigate to a detailed infusion record or infusion records which led server 20 to conclude that a reprogram event occurred.

FIG. 7 is a display screen of a hard limits override listing report, according to an illustrative embodiment. A hard limits override listing may display a list of Hard Limit Override infusions with the following information for each Hard Limit Override: Hard Limit Override Time, Location of pump that generated Hard Limit Override, Dataset used when Hard Limit Override occurred, Selected Profile used when Hard Limit Override occurred, Drug used when Hard Limit Override occurred, Hard Limit exceeded, etc. In this example, there are no hard limit overrides to report. A hard limit override may occur when a user attempts to program a parameter above a hard limit, for example, and the infusion pump instead programs the parameter at the hard limit, followed by a user confirmation and activation to start the infusion. Hard Limit Override Time will be selectable to navigate to the detailed Infusion Record during which the Hard Limit Override occurred.

Figure 8:
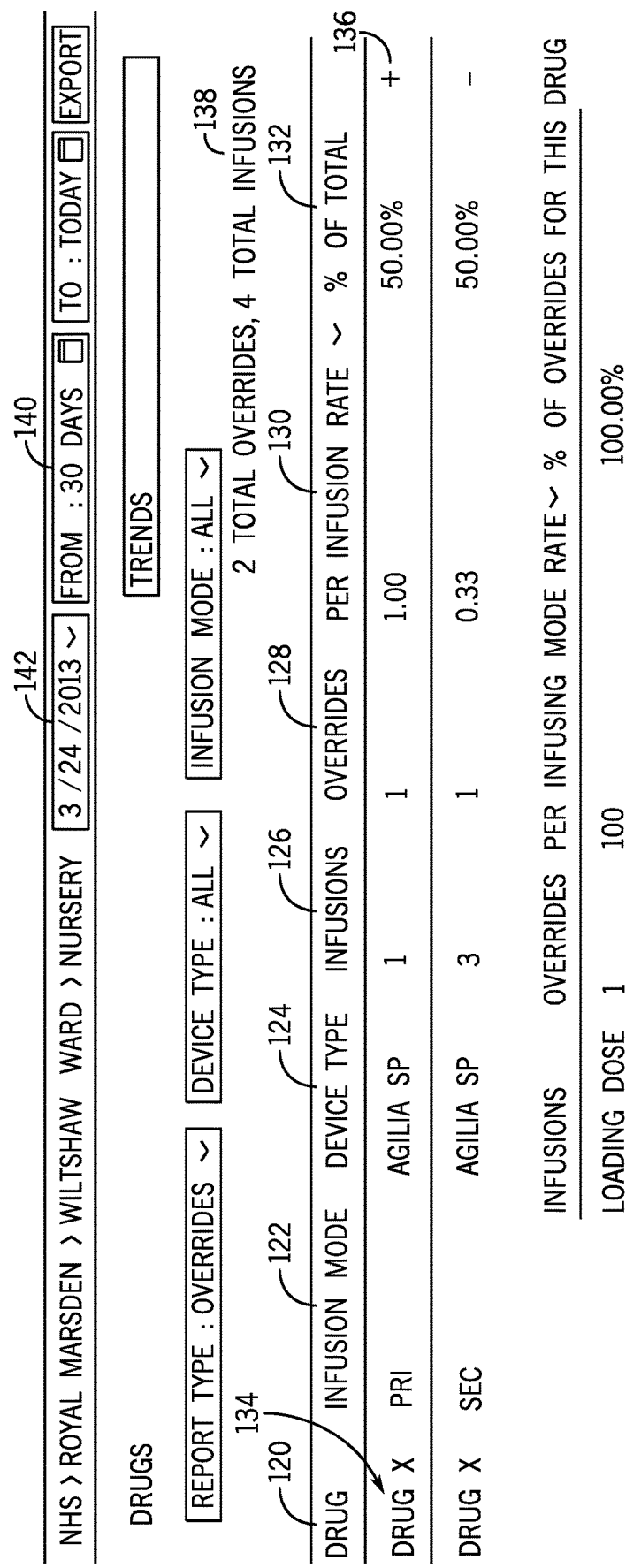
FIG. 8 is a display screen of a drug override report, according to an illustrative embodiment.

FIG. 8 is a display screen of a drug override report, according to an illustrative embodiment. The Drug Overrides report displays list of overrides by drug with the following information: Drug name 120, Infusion mode 122, Device type 124, Total number of infusions 126, Total number of Overrides 128, Overrides per infusion rate 130, and % of total Overrides 132. In one example 134, the drug is Drug X, in an infusion mode of primary infusion mode. The device type is an Agilia SP (a brand name for an infusion pump). The number of infusions of this drug in this mode for this device type is 1 and the number of overrides is 1. Server 20 is configured to calculate an override per infusion rate of 1.00 and a percent of total infusions of this drug as 50% (because another infusion of Drug X, as shown, had one out of three infusion modes based on an override.) An expansion input device 136 may be selected by a user to provide additional information regarding drug overrides reported. For example, clicking on the expansion input device 136 may show a breakdown of overrides based on infusion mode (e.g., loading dose, etc.). The display screen may also display a total number of overrides and total number of infusions 138 for the drug, time period 140 and/or dataset 142 selected.

Figure 9:
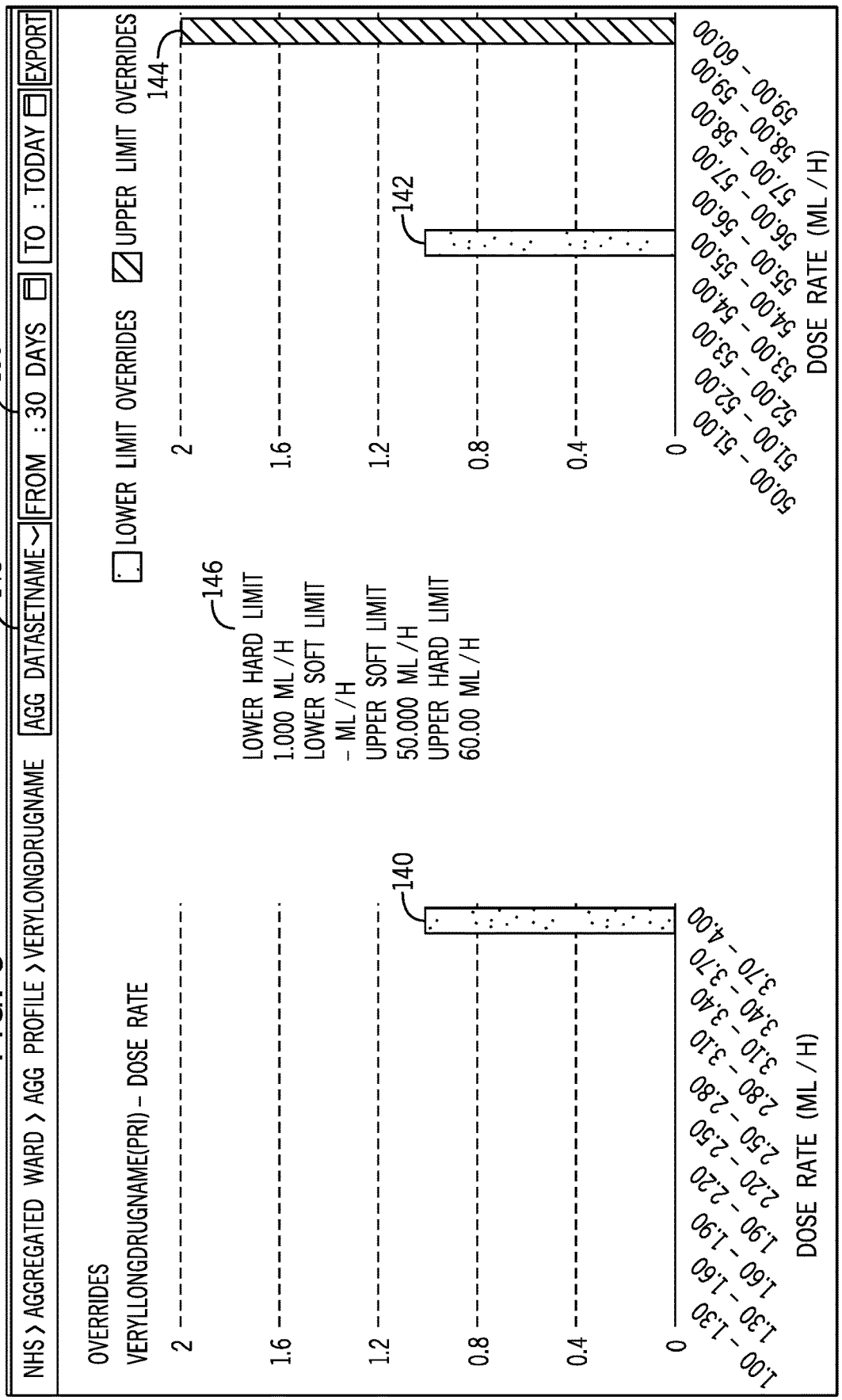
FIG. 9 is a display screen of a drug overrides limit chart report, according to an illustrative embodiment.

FIG. 9 is a display screen of a drug overrides limit chart report, according to an illustrative embodiment. The drug overrides limit chart report may displays one or more charts of overrides against hard and/or soft limits for a selected drug. In this embodiment, lower limit overrides 140, 142 are displayed separately from upper limit overrides 144. The limit charts may be displayed as histogram bar charts that group overrides into a plurality of bars (e.g., 10 bars) for the range between soft and hard limits (as shown in the X axes of the charts). In addition, the chart may display hard and soft limit values at a field 146, again for the selected drug, data set 148, and/or time period 150. The selected parameter is dose rate.

Figure 10:
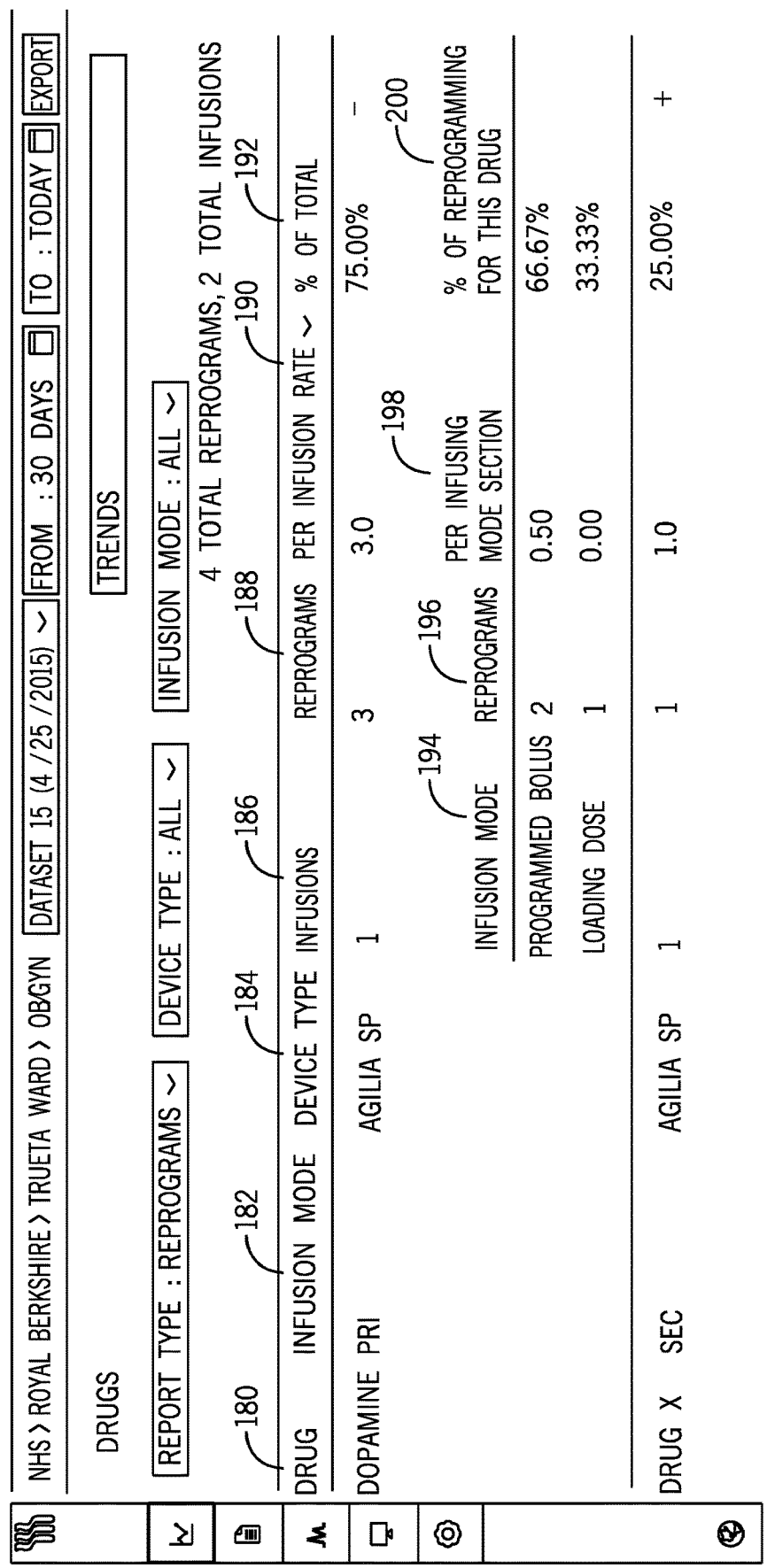
FIG. 10 is a display screen of a drug reprograms report, according to an illustrative embodiment.

FIG. 10 is a display screen of a drug reprograms report, according to an illustrative embodiment. A drug reprograms report will display a list of reprograms by drug with the following information: Drug name 180, Infusion mode 182, Device type 184, Total number of infusions 186, Total number of Reprograms 188, Reprograms per infusion rate 190 and % of total Reprograms 192. Each drug can be expanded using input device 193 to show additional information about drug reprograms grouped by infusion mode: (1) infusion mode 194; (2) number of Reprograms 196; (3) Reprograms per infusion rate 198; and (4) % of total Reprograms 200. Information in columns (1) Infusions and (2) Reprograms may be displayed as selectable links that a user may select to navigate to a pre-filtered report by location, Dataset, Profile, Drug, Device Type and/or Infusion Mode.

Figure 11:
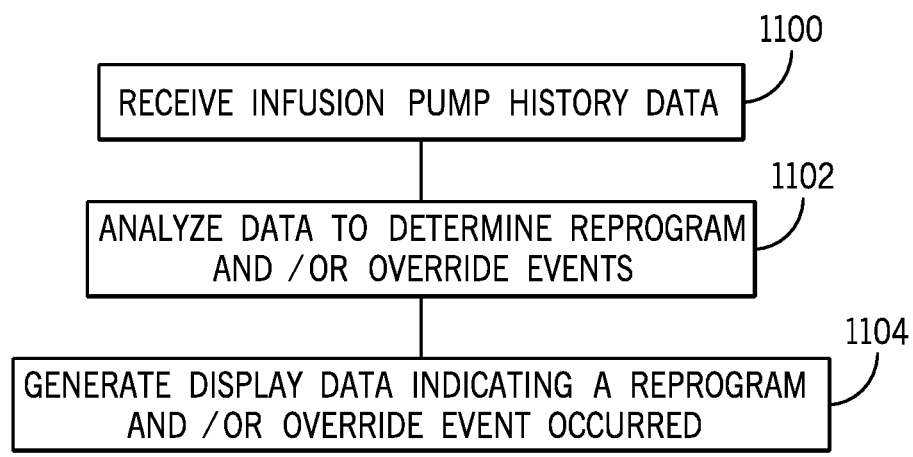
FIG. 11 is a flowchart of a method of processing infusion pump data for presentation on a display, according to an illustrative embodiment.

FIG. 11 is a flowchart of a method of processing infusion pump data for presentation on a display, according to an illustrative embodiment. At a block 1100, server computer 20 is configured to receive infusion pump history data from a plurality of infusion pumps over a network interface circuit. In one embodiment, the infusion pump history data may comprise an indication that a user inputted to an infusion pump a parameter which was outside of a prestored limit. This indication may be in the form of data, a flag, a field, a data structure, a value, a data file, or other data element that a computing device, such as server 20, may read to receive the indication. The indication may be generated by the infusion pump 10 that was controlled by the user with the parameter. The history data may further indicate that the user was notified that the value was outside of the limit, e.g., by way of a confirmation screen, alert, etc. The history data may further comprise an indication that the infusion pump parameter was returned to within the prestored limit (e.g., by the user scrolling to a new value within the limit, by the user confirming a suggested value within the limit by the pump, etc.). This return of the value may have occurred automatically, without requiring user input, or may have been done manually by the user. The return to within the limit may be at or below the prestored limit. This indication may be a discrete event reported or part of another event reported (e.g., a pump start event). The history data may further comprise an indication that the user started infusion on the pump at the parameter within the prestored limit. The activation may be a request to being or start an infusion, or another activation of the pump.

At a block 1102, the history data received is analyzed by server 20 to determine whether a reprogram event occurred. For example, server 20 may compare the history data received to determine whether a parameter was requested to be outside a soft limit, the parameter was returned to at or below the soft limit, and the pump began pumping. If the server 20 determines the three steps occurred, the server 20 may be configured to determine that a reprogram event occurred, and store an indication of such in memory.

At a block 1104, the server 20 may be configured to generate display data for presentation on a display, the display data indicating that a reprogram event occurred. The display data may be generated by an application program running on server 20 or another computer in communication with server 20. The display data may be sent to a display device for display. The display data may be generated in response to a user request, or in response to an automated process programmed by server 20. The display data may be formatted for any of a variety of types of displays, such as a text display, a graphical display, small or large displays, handheld mobile devices, liquid crystal displays, etc.

While this method is described with reference to a reprogram event, it may be modified to determine override events as described herein, regular infusion events, or one or more of reprogram, override and regular infusion events (e.g., infusion events that do not occur based on an override or reprogram event). The method may further be modified to analyze received infusion data for generation of any one or more of the display screens and reports described herein.

Figure 12:
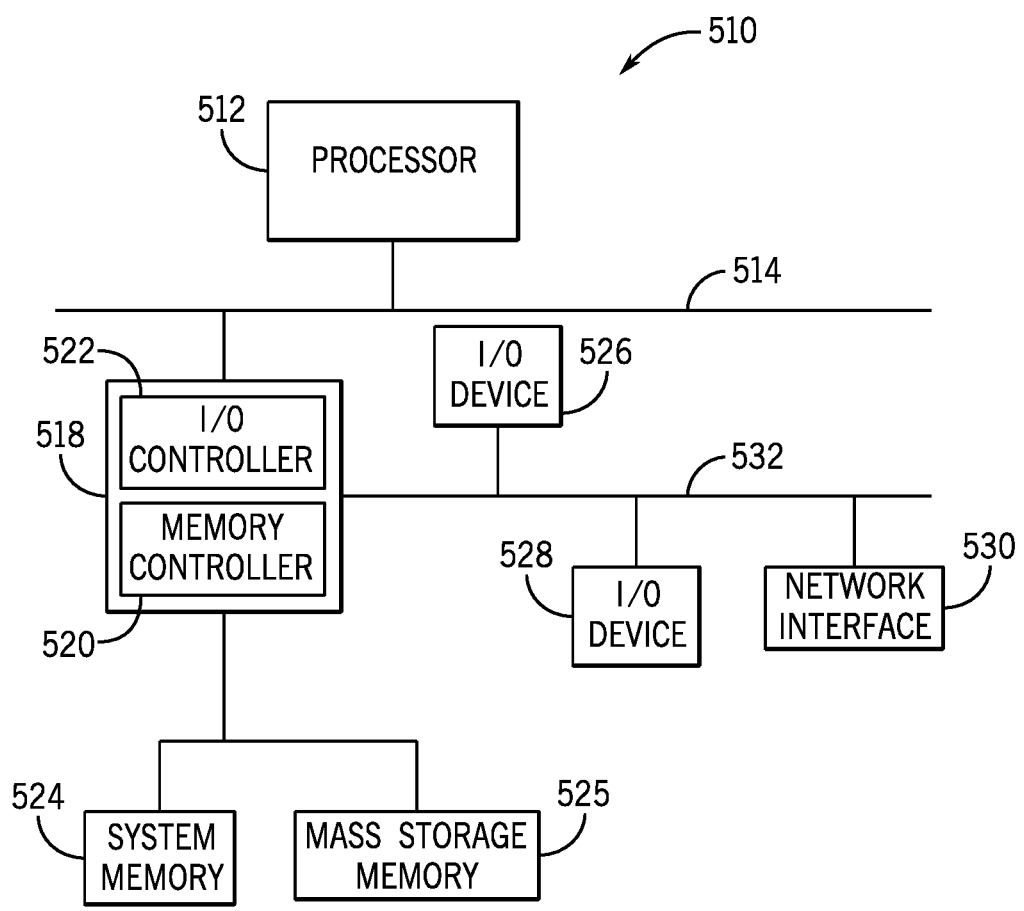
FIG. 12 is a block diagram of a server computer for processing infusion pump data for presentation on a display, according to an illustrative embodiment.

FIG. 12 is a block diagram of a server computer for processing infusion pump data for presentation on a display, according to an illustrative embodiment. In alternate embodiments, the systems and methods described herein may be implemented on a single server computer, a plurality of server computers, a server farm, a cloud server environment, or using other computer resources. Server 20 and infusion pump 10 may comprise analog and/or digital circuit components forming processing circuits configured to perform the steps described herein. The processing circuits may comprises discrete circuit elements and/or programmed integrated circuits, such as one or more microprocessors, microcontrollers, analog-to-digital converters, application-specific integrated circuits (ASICs), programmable logic, printed circuit boards, and/or other circuit components. Server 20 and infusion pump 10 each may comprise a network interface circuit configured to provide communications over one or more networks with each other and/or with other device. The network interface circuit may comprise digital and/or analog circuit components configured to perform network communications functions. The networks may comprise one or more of a wide variety of networks, such as wired or wireless networks, wide area-local-area or personal-area networks, proprietary or standards-based networks, etc. The networks may comprise networks such as an Ethernet network, networks operated according to Bluetooth protocols, IEEE 802.11x protocols, cellular (TDMA, CDMA, GSM) networks, or other network protocols. The network interface circuits may be configured for communication of one or more of these networks and may be implemented in one or more different sub-circuits, such as network communication cards, internal or external communication modules, etc.

According to one embodiment, storage of the infusion data records may be implemented on a database coupled to or part of server 20. The database may be a DBMS hosted on a server host platform, such as Microsoft Windows XP, Microsoft Windows Server 2008, etc.

Referring again to FIG. 12, a block diagram of an example processor system 510 is shown that can be used to implement systems, articles of manufacture, and methods described herein. As shown in FIG. 12, the processor system 510 includes a processor 512 that is coupled to an interconnection bus 514. The processor 512 can be any suitable processor, processing unit, or microprocessor, for example.

Although not shown in FIG. 12, the system 510 can be a multi-processor system and, thus, can include one or more additional processors that are identical or similar to the processor 512 and that are communicatively coupled to the interconnection bus 514.

The processor 512 of FIG. 12 is coupled to a chipset 518, which includes a memory controller 520 and an input/output ("I/O") controller 522. A chipset may provide I/O and memory management functions as well as a plurality of general purpose and/or special purpose registers, timers, etc. that are accessible or used by one or more processors coupled to the chipset 518. The memory controller 520 performs functions that enable the processor circuit 512 (or processors if there are multiple processors) to access a system memory 524 and a mass storage memory 525.

The system memory 524 can include any desired type of volatile and/or non-volatile memory such as, for example, static random access memory (SRAM), dynamic random access memory (DRAM), flash memory, read-only memory (ROM), etc. The mass storage memory 525 can include any desired type of mass storage device including hard disk drives, optical drives, tape storage devices, etc.

The I/O controller 522 performs functions that enable the processor 512 to communicate with peripheral input/output ("I/O") devices 526 and 528 and a network interface 530 via an I/O bus 532. The I/O devices 526 and 528 can be any desired type of I/O device such as, for example, a keyboard, a video display or monitor, a mouse, etc. The network interface 530 can be, for example, an Ethernet device, an asynchronous transfer mode device, an 802.11 device, a DSL modem, a cable modem, a cellular modem, etc. that enables the processor system 510 to communicate with another processor system.

While the memory controller 520 and the I/O controller 522 are depicted in FIG. 12 as separate blocks within the chipset 518, the functions performed by these blocks can be integrated within a single semiconductor circuit or can be implemented using two or more separate integrated circuits.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a tangible machine accessible or readable medium and executable by, for example, a processor system (e.g., the example processor system 510 of FIG. 12). Tangible computer readable media include a memory, DVD, CD, etc. storing the software and/or firmware, but do not include a propagating signal.

As used herein, the term tangible computer readable medium includes any type of computer readable storage and excludes propagating signals. Additionally or alternatively, the example processes described herein may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information).

Certain embodiments described herein can omit one or more of the method steps and/or perform the steps in a different order than the order listed. For example, some steps cannot be performed in certain embodiments. As a further example, certain steps can be performed in a different temporal order, including simultaneously, than listed above.

While the embodiments have been described with reference to certain details, it will be understood by those skilled in the art that various changes can be made and equivalents can be substituted without departing from the scope described herein. In addition, many modifications can be made to adapt a particular situation or material to the teachings without departing from its scope. Therefore, it is intended that the teachings herein not be limited to the particular embodiments disclosed, but rather include additional embodiments falling within the scope of the appended claims.

The invention claimed is:

1. A method of processing infusion pump data for presentation on a display, comprising:
   receiving infusion pump history data from a plurality of infusion pumps over a network interface circuit, the infusion pump history data comprising:
      an indication that a user inputted to an infusion pump a parameter which was outside of a prestored limit,
      an indication that the user was notified that the parameter was outside the prestored limit;
      an indication that the infusion pump parameter was returned to within the prestored limit, and an indication that the user started infusion on the pump at the parameter within the prestored limit;
   determining that an event occurred based on the indications that the user inputted the parameter outside of the prestored limit, the user was then notified, the parameter was then returned to within the prestored limit and the user then started infusion on the pump at the parameter within the prestored limit;
   generating display data for presentation on a display to a second user, the display data indicating a number of the events that occurred for a drug;
   after generating the display data, receiving a change from the second user to a data set comprising hard limits and soft limits for pump programming parameters;
   downloading the changed data set to the infusion pump to program the infusion pump with the changed data set based on the received change; and
   administering the drug to a patient pursuant to parameters entered by a clinician into the infusion pump and using the changed data set.

2. The method of claim 1, wherein the display data further comprises a time that the user started infusion on the pump, a care area within a medical facility associated with the infusion pump and a drug name of a drug that was administered when the user started infusion on the pump.

3. The method of claim 1, further comprising receiving a user selection of a drug name and generating display data indicating a plurality of reprogram events that occurred for the selected drug name.

4. The method of claim 1, wherein the infusion pump history data further comprises:
   an indication that the user inputted a parameter which was within the prestored limit, and
   an indication that the user started infusion on the pump at the parameter within the prestored limit;
   further comprising:
   determining that an infusion event occurred based on an analysis of the indications that the user inputted a parameter which was within the prestored limit, and the indication that the user started infusion on the pump at the parameter within the prestored limit; and generating display data indicating the infusion event.

5. The method of claim 4, further comprising generating display data indicating the number of events and a number of infusion events.

6. The method of claim 5, further comprising generating display data indicating a rate or percentage of reprogram events to infusion events.

7. The method of claim 4, wherein the display data indicating the infusion event and the display data indicating the event are both selectable to show a report of respective events filtered by at least one of care area, drug, device type and infusion mode.

8. The method of claim 1, wherein the infusion pump history data further comprises:

an indication that a user started infusion on the pump at the parameter which was outside of the prestored limit;

further comprising determining that an override event occurred based on the analysis of the infusion pump history data, wherein the display data indicates that an override event occurred.

9. The method of claim 1, further comprising a plurality of infusion pumps in communications with the server computer.

* * * * *